(12) United States Patent
Whelan

(10) Patent No.: US 11,284,961 B2
(45) Date of Patent: Mar. 29, 2022

(54) SHARPS PASSING TRAY

(71) Applicant: NOBLE HOUSE GROUP PTY. LTD., Chelsea Heights (AU)

(72) Inventor: Chris Whelan, Leichhardt (AU)

(73) Assignee: NOBLE HOUSE GROUP PTY. LTD.

( * ) Notice: Subject to any disclaimer, the term of this patent is extended or adjusted under 35 U.S.C. 154(b) by 355 days.

(21) Appl. No.: 16/307,504

(22) PCT Filed: Jun. 6, 2017

(86) PCT No.: PCT/AU2017/050561
§ 371 (c)(1),
(2) Date: Dec. 6, 2018

(87) PCT Pub. No.: WO2017/210732
PCT Pub. Date: Dec. 14, 2017

(65) Prior Publication Data
US 2019/0307525 A1    Oct. 10, 2019

Related U.S. Application Data

(60) Provisional application No. 62/345,931, filed on Jun. 6, 2016.

(51) Int. Cl.
*A61B 50/33* (2016.01)
*A61B 50/20* (2016.01)
(Continued)

(52) U.S. Cl.
CPC .............. *A61B 50/33* (2016.02); *A61B 50/20* (2016.02); *A61B 50/3001* (2016.02); *A61B 2090/0801* (2016.02)

(58) Field of Classification Search
CPC ..... A61B 50/33; A61B 50/20; A61B 50/3001; A61B 2090/0801
(Continued)

(56) References Cited

U.S. PATENT DOCUMENTS 3,013,656 A * 12/1961 Murphy, Jr. ......... B65D 81/027
                                                    206/572
3,983,996 A * 10/1976 Hendren, III ....... A61M 25/002
                                                    206/363

(Continued)

FOREIGN PATENT DOCUMENTS

AU          343287       7/2012
AU       2012203428      1/2014

*Primary Examiner* — Jacob K Ackun
(74) *Attorney, Agent, or Firm* — Galbreath Law Offices, P.C.; John A. Galbreath

(57) ABSTRACT

A medical tray (10) is adapted to receive a medical instrument (90) and has one or more longitudinally extending instrument receiving recesses (22) adapted to receive at least a part of the medical instrument (90), one or more instrument support members (30, 32, 36, 38, 40, 82) and at least one instrument access opening, slot or recess (86) at a longitudinal end of a peripheral wall, whereby the instrument (90) may be located longitudinally in the tray (10) with at least part (92) of the instrument supported on one or more instrument support members (30, 32, 36, 38, 40, 82), another part (94) may extend out of the tray via the instrument access opening (86) with a cutting edge or point of the medical instrument located in at least one instrument receiving recess (22).

15 Claims, 9 Drawing Sheets

(51) Int. Cl.
*A61B 50/30* (2016.01)
*A61B 90/00* (2016.01)

(58) Field of Classification Search
USPC .............................. 206/363, 365, 366, 370
See application file for complete search history.

(56) References Cited

U.S. PATENT DOCUMENTS

| | | | | |
|---|---|---|---|---|
| 4,153,160 | A * | 5/1979 | Leigh | A61B 50/33 206/370 |
| 4,324,331 | A * | 4/1982 | Ignasiak | A61L 2/26 206/363 |
| 4,915,233 | A * | 4/1990 | Smith | A61M 5/008 206/366 |
| 5,024,326 | A * | 6/1991 | Sandel | A61B 50/3001 206/363 |
| 5,339,955 | A | 8/1994 | Horan | |
| 5,368,580 | A * | 11/1994 | Suzuki | A61M 5/3216 206/365 |
| 5,441,152 | A * | 8/1995 | Estes | B25H 3/006 206/349 |
| 5,542,533 | A | 8/1996 | Vargas, III | |
| 6,065,596 | A * | 5/2000 | Cavanagh | A61B 50/20 206/352 |
| 6,216,885 | B1 * | 4/2001 | Guillaume | A61M 5/008 206/366 |
| 6,405,863 | B1 * | 6/2002 | Dhindsa | B65D 1/36 206/370 |
| RE40,432 | E | 7/2008 | Cavanagh | |
| 7,441,655 | B1 * | 10/2008 | Hoftman | A61B 50/20 206/370 |
| 8,317,028 | B2 * | 11/2012 | Doster | B65D 5/503 206/564 |
| 2006/0042977 | A1 | 3/2006 | Sandel | |
| 2006/0091031 | A1 * | 5/2006 | Bowen | B25H 3/06 206/372 |
| 2008/0045861 | A1 * | 2/2008 | Miller | A61B 46/10 600/567 |
| 2014/0001067 | A1 | 1/2014 | Gitman | |
| 2019/0105122 | A1 * | 4/2019 | Miller | A61B 10/025 |

* cited by examiner

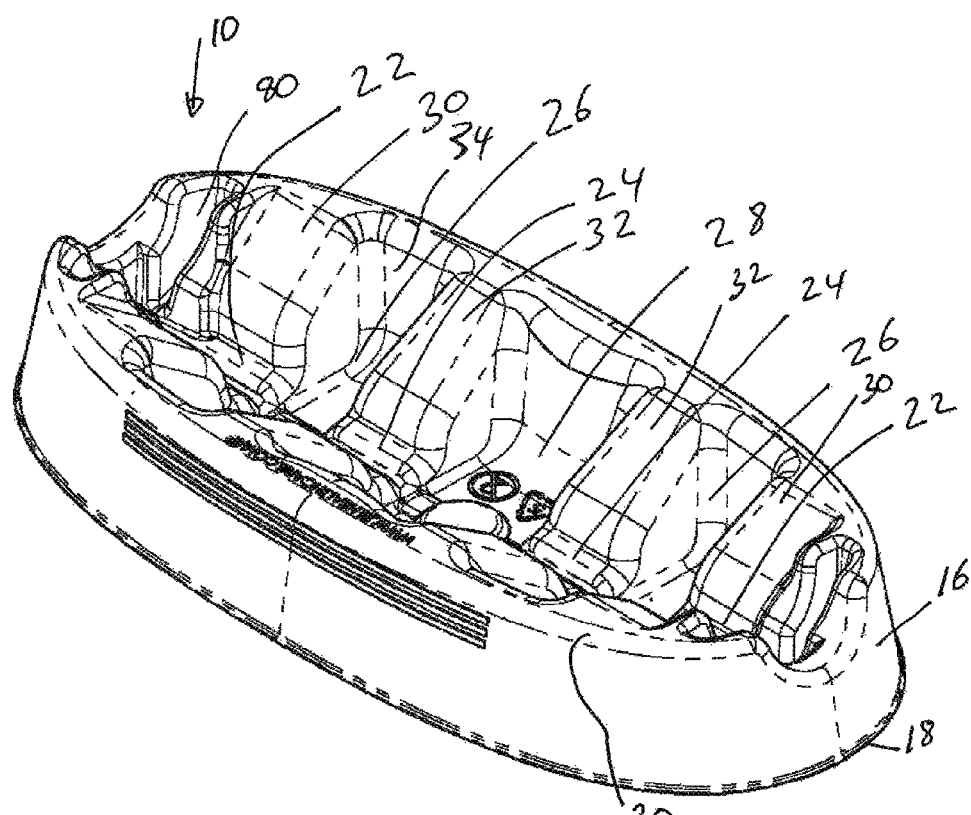
Figure 1
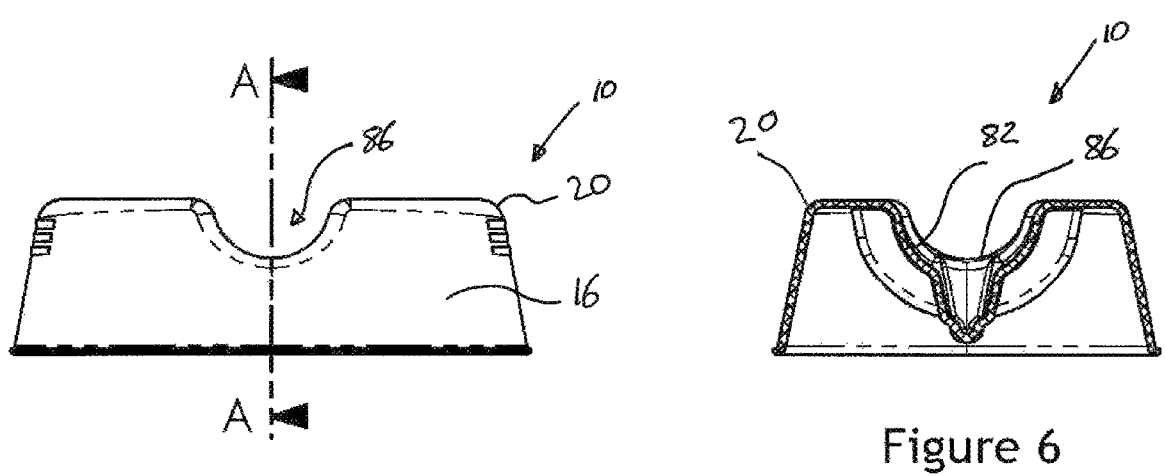
Figure 4
Figure 6

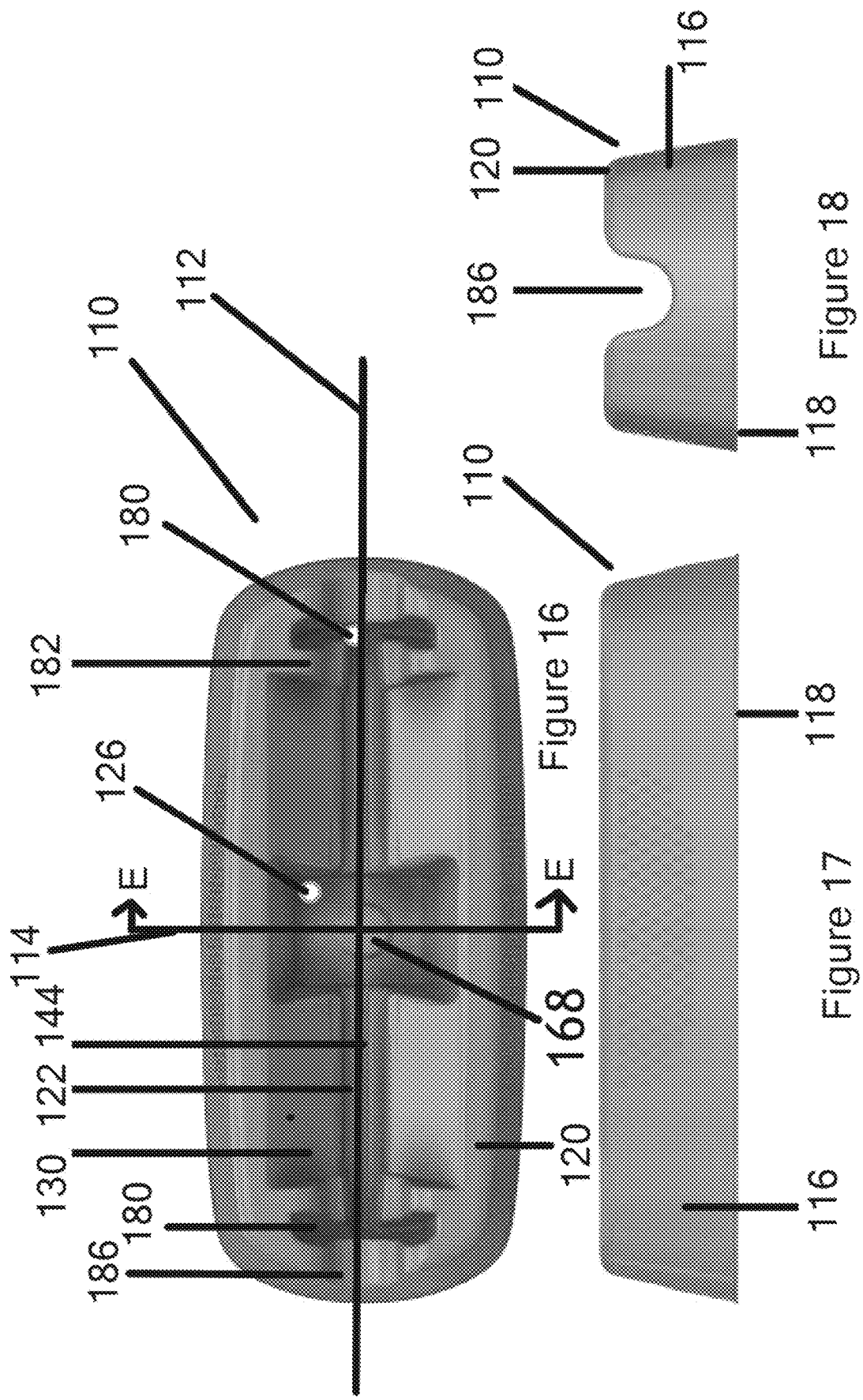

SHARPS PASSING TRAY

FIELD OF INVENTION

This invention relates to trays for medical instruments and more particularly to trays that are used to temporarily store or hold medical instruments capable of cutting or piercing a person's skin, such as a scalpel, a straight or curved medical stitching needle or a cannula mounted on a syringe or part of medical apparatus such as an apheresis kit.

BACKGROUND

During medical procedures a medical instrument such as a scalpel or medical needle may be temporarily placed in a tray. This may be because a medical practitioner will reuse the instrument during the medical procedure or as a temporary storage location after removal from a patient.

SUMMARY OF THE INVENTION

The present invention provides a medical tray adapted to receive a medical instrument, the tray having:
a longitudinal axis;
at least one set of a first longitudinally extending primary instrument receiving recess, a second longitudinally extending primary instrument receiving recess and a longitudinally extending finger recess;
the first and second primary instrument receiving recesses adapted to receive at least a part of the medical instrument and being spaced apart along the longitudinal axis with the finger recess between the first and second primary instrument receiving recesses and having a transverse width greater than at least one of the first and second instrument receiving recesses.

The finger recess may extend below at least one of the first and second primary instrument receiving recesses.

The tray may include:
at least one instrument support member and
at least one instrument access opening, slot or recess at a longitudinal end of a peripheral wall, whereby
an instrument may be located longitudinally in the tray with at least part of the instrument supported on at least one of the at least one instrument support member, another part may extend out of the tray via the at least one instrument access opening with a cutting edge or point of the medical instrument located in an instrument receiving recess.

The present invention also provides a medical tray adapted to receive a medical instrument, the tray having:
a longitudinal axis;
at least one longitudinally extending primary instrument receiving recess adapted to receive at least a part of the medical instrument;
at least one instrument support member and
at least one instrument access opening, slot or recess at a longitudinal end of a peripheral wall, whereby
an instrument may be located longitudinally in the tray with at least part of the instrument supported on at least one of the at least one instrument support member, another part may extend out of the tray via the at least one instrument access opening with a cutting edge or point of the medical instrument located in at least one primary instrument receiving recess.

The at least one longitudinally extending primary instrument receiving recess may comprise at least one set of longitudinally extending primary instrument receiving recesses, each set comprising a first longitudinally extending primary instrument receiving recess and a second longitudinally extending primary instrument receiving recess.

The tray may also comprise a longitudinally extending finger recess.

Where the tray comprises first and second primary instrument receiving recesses and a finger recess the first and second primary instrument receiving recesses may be spaced apart along the longitudinal axis with the finger recess between the first and second primary instrument receiving recesses.

The finger recess may have a transverse width greater than at least one of the first and second primary instrument receiving recesses.

The tray may include two sets of the first and second primary instrument receiving and finger recesses, with the two sets extending in opposite directions along the longitudinal axis with the first primary instrument receiving recesses spaced further apart than the second primary instrument receiving recesses.

A central finger recess may be provided between the two second primary instrument receiving recesses.

The central finger recess may have a transverse width greater than at least one of the first and second primary instrument receiving recesses.

The first primary instrument receiving recess may be closed at an end remote from the finger recess.

The first primary instrument receiving recess may have a first base section.

The second primary instrument receiving recess may have a second base section.

The base section of either or both of the first and second primary instrument receiving recesses may include two opposed first base wall portions that extend transversely in opposite directions. The two first base wall portions may define a non-planar base. The two first base wall portions may be generally planar and may be angled to each other. Alternatively the two first base wall portions may be curved and extend away from each other to define a base portion that becomes wider from its base.

The base section of either or both of the first and second primary instrument receiving recesses may include at least one secondary recess for receiving a small medical instrument, such as a needle. Where the first base section includes only one secondary recess the secondary recess may be located centrally of the recess or located centrally of the axis, but may be located off-centre. There may be two or more secondary recesses.

Where the first or second instrument receiving recess has two first base wall portions the at least one secondary recess may be formed in at least one of the first base wall portions. The at least one secondary recess may be formed between the two first base wall portions.

Where the tray includes a central finger recess the central finger recess may extend below at least one of the first and second recesses. The central finger recess may include a portion that is aligned with a part of the first or second recesses. Where the tray includes at least one secondary recess the central finger recess may include a portion that is aligned with the at least one secondary recess.

The tray may include at least one guide member to assist location of a medical instrument in at least one instrument receiving recesses.

At least one guide member may extend transversely from a first instrument receiving recess.

At least one guide member may extend transversely from a second instrument receiving recess.

The at least one guide member may extend from an upper region of an instrument receiving recess to the periphery of the tray. The at least one guide member may extend from an upper region of an instrument receiving recess to the periphery of the tray at an angle so that, in use, a medical instrument placed on a guide member will move under the action of gravity toward an instrument receiving recess.

Each or both of the first and second instrument receiving recesses may each have two guide members extending in opposite transverse directions.

Where the tray includes a plurality of guide members the guide members may extend at the same or different angles to each other.

Where the tray includes a plurality of guide members the guide members may be co-planar or non-co-planar. The guide members may connect to the instrument receiving recesses.

Where the guide members connect to the instrument receiving recesses they may do so at the same or different distances from a base of the tray from each other.

The tray may include a peripheral region. In plan view the peripheral region may extend around the at least one instrument receiving recess (and if present, the finger recesses) in a closed loop. The majority of the peripheral region may define an upper edge or edges that lie in a plane equidistant from the base of the tray, i.e. in a horizontal plane in use.

The tray may include at least one additional instrument receiving portion located between a first instrument receiving recesses and the peripheral region. The at least one additional instrument receiving portion may be connected to the first instrument receiving recess. The additional instrument receiving portion may extend transversely in both directions from the longitudinal axis. The additional instrument receiving portion is preferably sized to receive a finger flange of a syringe The peripheral region may include an instrument access opening that is nearer the base than the majority of the peripheral region. The instrument access opening may, in end view, be curved and more particularly semicircular. The instrument access opening is preferably sized so that when a syringe is located in the tray with its finger flange in the additional instrument receiving portion(s), the plunger of the syringe may extend out of the tray above or through the instrument access opening without contacting the peripheral region.

The peripheral region may, in plan view, define an oval or oval like shape but may be other shapes.

BRIEF DESCRIPTION OF THE DRAWINGS

FIG. 1 is a perspective view of a tray according to a first embodiment of the invention.

FIG. 4 is an end view of the tray of FIG. 1.

FIG. 6 is an end cross sectional view of the tray of FIG. 1 taken along line BB in FIG. 5.

FIG. 16 is a plan view of the tray of FIG. 15.

FIG. 17 is a side view of the tray of FIG. 15.

FIG. 18 is an end view of the tray of FIG. 15.

DETAILED DESCRIPTION OF PREFERRED AND OTHER EMBODIMENTS

Figure 2:
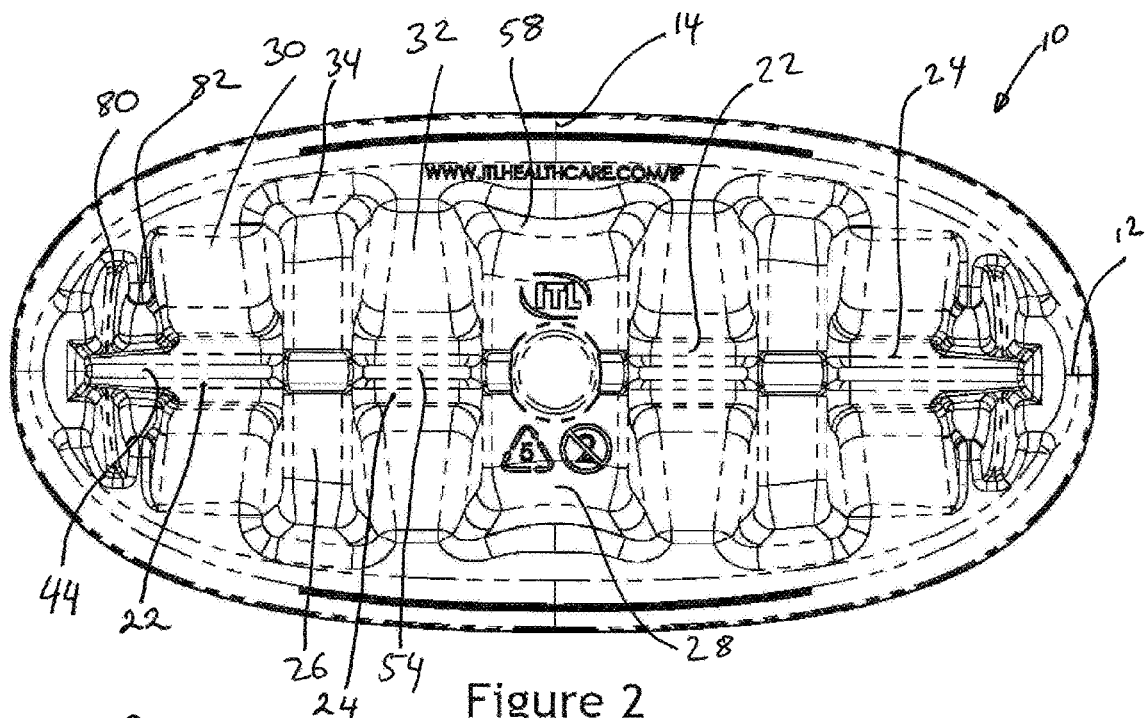
FIG. 2 is a plan view of the tray of FIG. 1.
Figure 3:
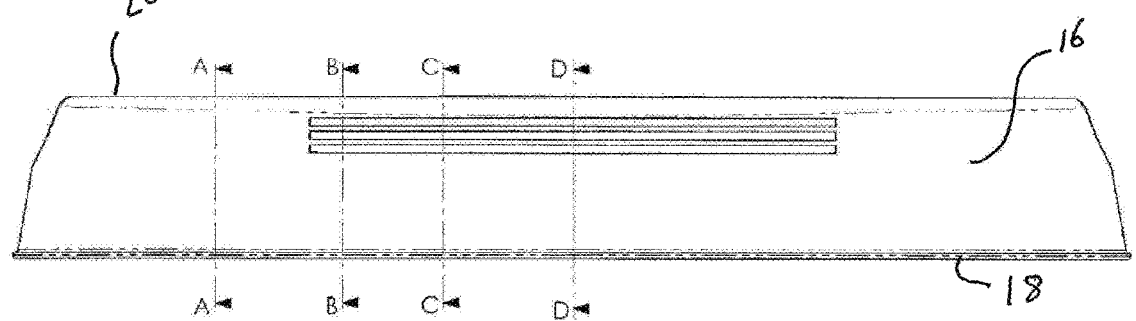
FIG. 3 is a side view of the tray of FIG. 1.
Figure 5:
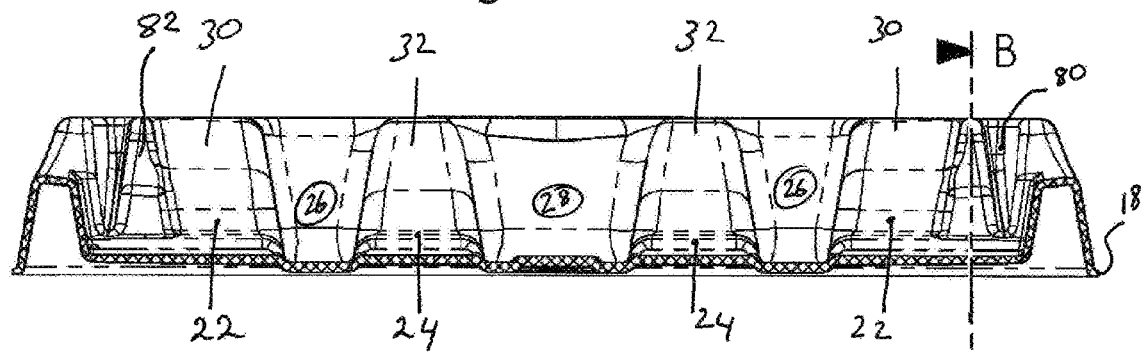
FIG. 5 is a side cross sectional view of the tray of FIG. 1 taken along line AA in FIG. 4.

Referring to FIGS. 1 to 14 there is shown a sharps passing tray 10 according to a first implementation of the invention.

The tray 10 is preferably formed of thin walled plastics material and may be formed by vacuum or injection moulding, for example.

The tray 10 is generally symmetric about both its longitudinal axis 12 and transverse axis 14.

In plan view the tray has a generally oval like shape and is formed of a single wall 16 but may be rectangular if desired. The lower edge 18 of the wall 16 lies in a plane and forms the base upon which the tray is supported. The wall 16 extends upwards and slightly inwards from lower edge 18 to upper peripheral edge 20 and then extends inwards and generally downwards to the longitudinal axis 12. The peripheral edge 20 lies in a plane.

The tray has two sets 19 of longitudinally extending primary instrument receiving recesses. These are arranged end on end with the two sets extending in opposite directions from the transverse axis 14. Each set comprises a first primary instrument receiving recess 22 located toward the end of the tray and a second primary instrument receiving recess 24 located nearer to the transverse axis. The first and second primary instrument receiving recesses 22 and 24 of each set 19 are separated by a transverse extending finger recess 26 whilst the two second primary instrument receiving recesses 24 are separated by a central transverse extending finger recess 28.

The first and second primary instrument receiving recesses are generally U shaped with ramps 30 and 32 respectively extending transversely from their upper regions toward the peripheral edge 20.

The upper surface of each of ramps 30 and 32 extends inwards and downwards from peripheral edge 20 generally in a plane (i.e. they have a flat upper surface) but the upper surfaces may curve downwards, either with increasing or decreasing steepness (i.e. they may be flat, concave or convex).

Figure 7:
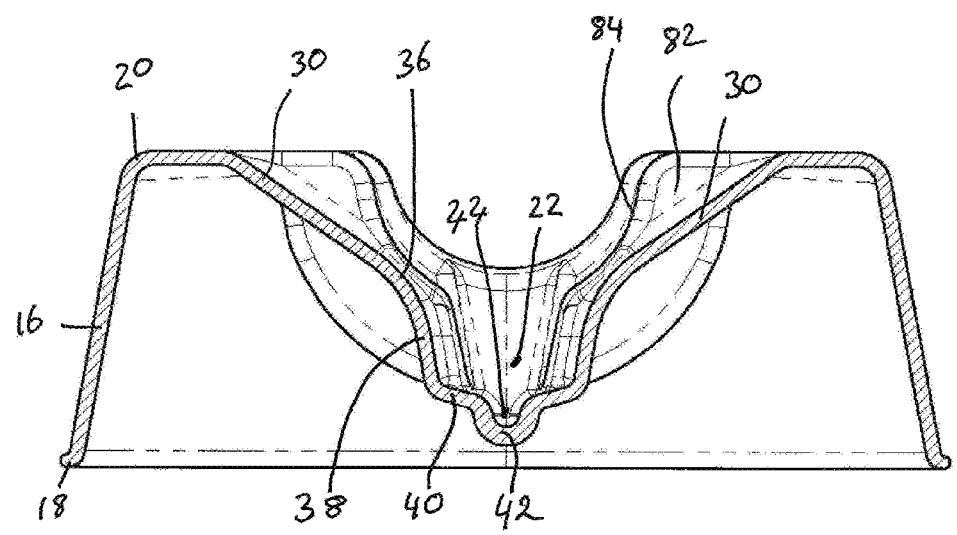
FIG. 7 is an end cross sectional view of the tray of FIG. 1 taken along line AA in FIG. 3.

FIG. 7 shows a cross-sectional view through the first primary instrument receiving recess 22 and ramps 30. The ramps 30 extend inwards and downwards and transition into recess 22 at curved portions 36 to steeper wall portions 38. Wall portions 38 are joined to less steep wall portions 40 which in turn join central wall portion 42 that defines, in cross section, a semicircular instrument receiving secondary recess 44. The wall portions 40 are angled upwards from central wall portion 42 toward wall portion 38 but each extends in a plane that, in the longitudinal direction, remains a generally constant distance from the plane of lower edge 18.

Figure 9:
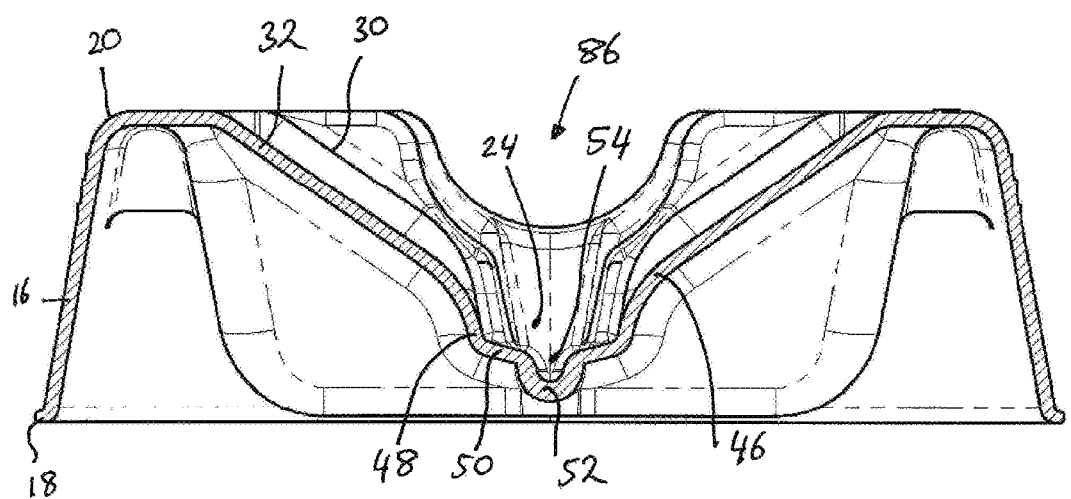
FIG. 9 is an end cross sectional view of the tray of FIG. 1 taken along line CC in FIG. 3.

FIG. 9 shows a cross-sectional view through the second instrument receiving recess 24 and ramps 32. In this embodiment the ramps 32 extend at generally the same angle as ramps 30. However, because the tray is wider at that longitudinal location the ramp 32 is lower as it transitions into recess 24 at 46 toward steeper wall portions 48. The transition 46 and wall portions 48 may be a continuously curved wall portion or a curved portion and a planar portion. Wall portions 48 join with less steep wall portions 50. Wall portions 50 joins with central wall portion 52 that defines, in cross section, a semicircular instrument receiving secondary recess 54.

As best seen in FIG. 9, wall portions 40 and 50 extend generally in a common plane, as do wall portions 42 and 52. The horizontal transverse extent of wall portions 50 is parallel to the longitudinal axis and generally the same as the horizontal transverse extent of wall portions 40 at the end nearer the ramp 60.

Figure 8:
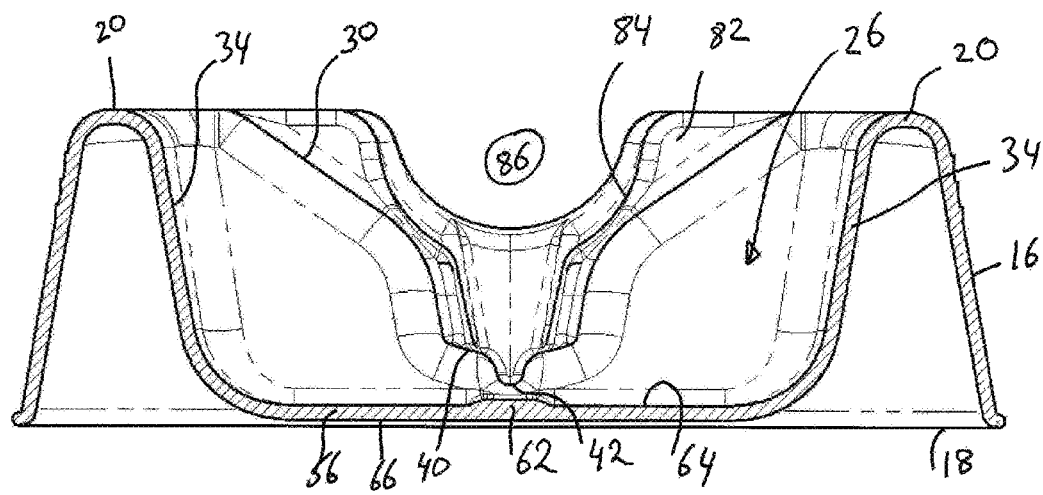
FIG. 8 is an end cross sectional view of the tray of FIG. 1 taken along line BB in FIG. 3.

Referring to FIG. 8, wall portions 34, which are located longitudinally between the ramps 30 and 32 (see FIGS. 1 and 2) extend steeply to base wall portion 56 and define the transverse extending finger recesses 26. Base wall portion 56 includes slightly thicker central portion 62. This is a flow leader for moulding purposes and may be omitted.

As best seen in FIG. 8 the upper surface 64 of wall portion 56 is below the lowermost points of wall portions 40, 42, 50 and 52 and so enables a user more easily to grasp an object located in the recess or central recess. The lower surface 66 of base wall 56 is generally planar but slightly raised compared to lower edge 18.

Figure 10:
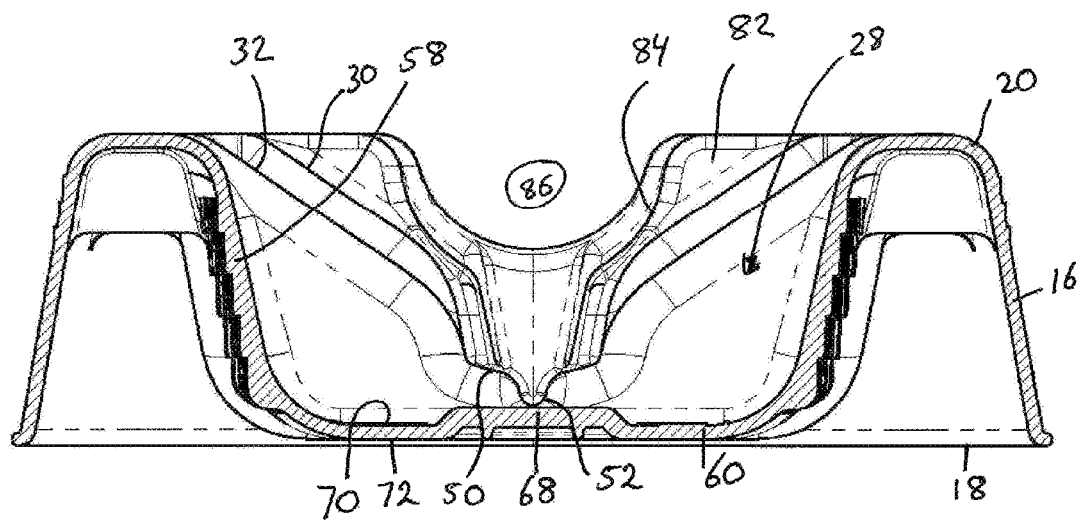
FIG. 10 is an end cross sectional view of the tray of FIG. 1 taken along line DD in FIG. 3.

Similarly, referring to FIG. 10, the wall portions 58 located longitudinally between the ramps 32 (see FIGS. 1 and 2) extend steeply to base wall portion 60 and define the central transverse extending finger recesses 28.

Base wall portion 60 includes slightly thicker central portion 68. Again this is a flow leader for moulding purposes and may be omitted.

As best seen in FIG. 10 the upper surface 70 of wall portion 60, including central surface 68, is at or below the lowermost points of wall portions 50 and 52. The lower surface 72 of base wall 56 lies generally in a plane but is slightly raised compared to lower edge 18.

The length of the tray is sized to enable a scalpel comprising a handle and blade to be stored temporarily in the tray. The user may place a scalpel on the ramps 30, 32 with the blade edge facing the centreline. The scalpel then slides down the ramps 30, 32 and falls into one or more of the instrument receiving recess 22 and 24 with the blade generally angled downwards and facing away from the user. The angled nature of the wall portions 40, 50 and the central further recesses 44 and 54 assist in this, with the lower edge of the scalpel handle being more likely to be received in one or more of the central secondary recesses and with the upper edge of the scalpel handle resting against one of the side walls portions 38, 48 or 46.

A needle may be temporarily placed in the tray and located partially in one or more of the secondary recesses 44 and 54. The secondary recesses 44 and 54 are sized so that the point of a needle located in these secondary recesses cannot be contacted by a user merely by placing a finger on the side wall portions 40 or 50. Preferably the longitudinal length of the secondary recesses 44 and 54 is such that at least part (preferably the blunt rear end) of a standard medical needle will extend out of the secondary recesses and into the finger recesses so as to enable a user to grasp that part when needed.

Figure 11:
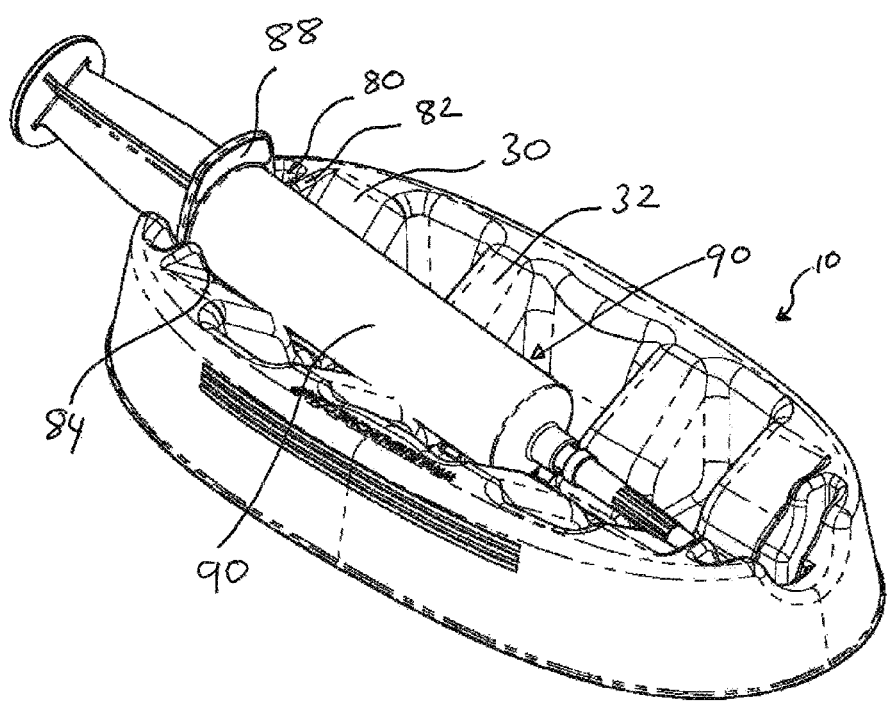
FIG. 11 is a perspective view of the tray of FIG. 1 with a syringe.
Figures 12, 13, 14:
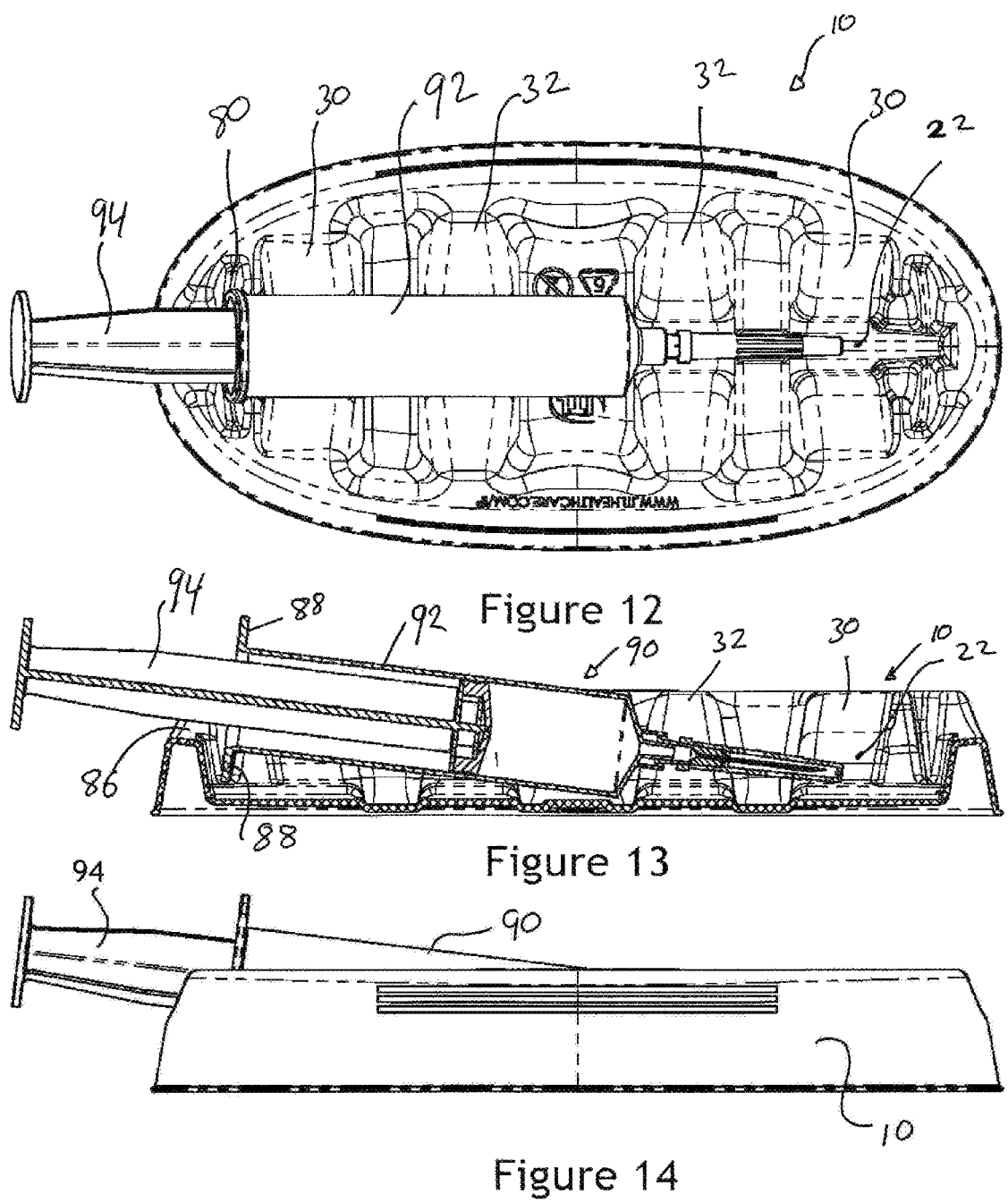
FIG. 12 is a plan view of the FIG. 12 arrangement.
FIG. 13 is a side cross sectional view of the FIG. 12 arrangement.
FIG. 14 is a side view of the FIG. 12 arrangement.
Figure 15:
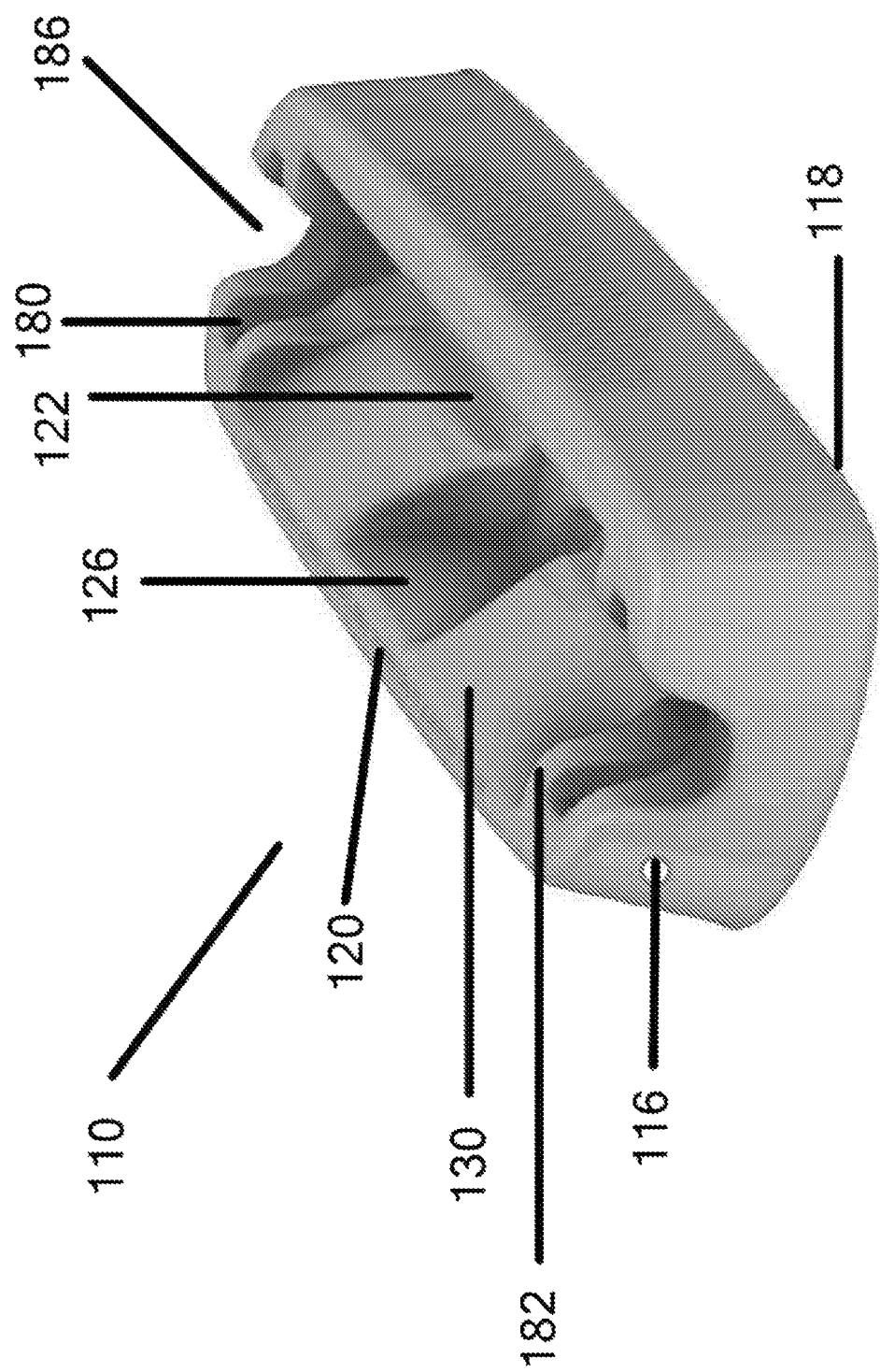
FIG. 15 is a perspective view of a tray according to a second embodiment of the invention.

As best seen in FIG. 2, each secondary recess 44 extends beyond the instrument receiving recess 22 and communicates with instrument flange slot or recess 80 that extends sideways from adjacent the closed end of secondary recess 44. The instrument flange recess 80 is delineated from ramp 22 by wall portion 82 which has curved surface 84. The peripheral wall 16 has a curved instrument access opening 86 at each of the ends of the tray, as best seen in FIG. 4. As best seen in FIGS. 11 to 13, the instrument flange recess 80 is sized and shaped to accommodate the finger flanges 88 of a syringe 90, with the barrel 92 supported in the tray by finger flanges 88 and/or parts of the barrel 92 resting on curved surface 84 and/or other portion(s) of the tray and generally located in recesses between ramps 30 and 32. The curved instrument access opening 86 allows the plunger 94 to extend out of the tray.

The angled ramps 30 and 32 serve to aid in centring the syringe in the tray when initially placed in the tray.

Whilst the secondary recess 44 extends beyond the instrument receiving recess 22 and communicates with instrument flange recess 80, it will be appreciated that this is not critical and wall portion 82 may form a barrier between the secondary recess 42 and instrument flange recess 80, with wall portion 82 having a single continuous curved surface portion.

Referring to FIGS. 15 to 20 there is shown a sharps passing tray 110 according to a second implementation of the invention. The tray 110 is similar to the tray of the first implementation.

The tray 110 is preferably formed of thin walled plastics material and may be formed by vacuum or injection moulding, for example.

The tray 110 is generally symmetric about both its longitudinal axis 112 and transverse axis 114.

In plan view the tray 110 has a generally oval like shape and is formed of a single wall 116 but may be rectangular if desired. The lower edge 118 of the wall 116 lies in a plane and forms the base upon which the tray is supported. The wall 116 extends upwards and slightly inwards from lower edge 118 to upper peripheral edge 120 and then extends inwards and generally downwards to the longitudinal axis 112. Upper peripheral edge 120 lies in a plane.

The tray has a pair of longitudinally extending primary instrument receiving recesses 122 extending in opposite directions from the transverse axis 114. The primary instrument receiving recesses 122 are separated by a transverse extending finger recess 126.

The primary instrument receiving recesses are generally U shaped with ramps 130 respectively extending transversely from their upper regions toward the peripheral edge 120.

The upper surface of ramps 130 extends inwards and downwards from peripheral edge 120 generally in a plane (i.e. they have a flat upper surface) but the upper surfaces may curve downwards, either with increasing or decreasing steepness (i.e. they may be flat, concave or convex).

Figure 19:
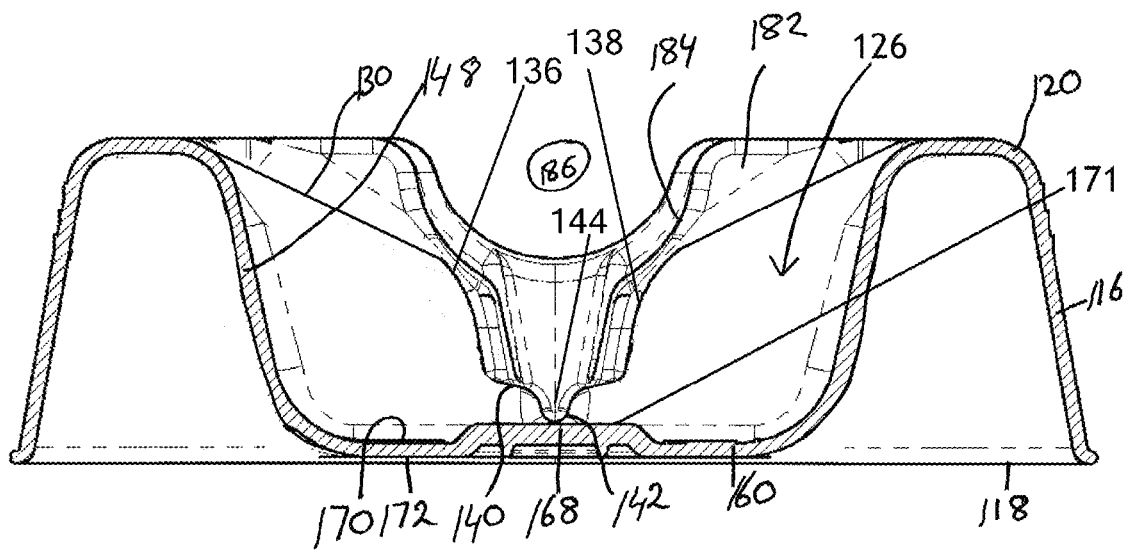
FIG. 19 is an end cross sectional view of the tray of FIG. 15 taken along line EE in FIG. 15.

FIG. 19 shows a central cross-sectional view showing the primary instrument receiving recess 122 and ramps 130. The ramps 130 extend inwards and downwards and transition into recess 122 at curved portions 136 to steeper wall portions 138. Wall portions 138 are joined to less steep wall portions 140 which in turn are joined to central wall portion 142. Central wall portion 142 defines, in cross section, a semicircular secondary instrument receiving recess 144. The wall portions 140 are angled upwards from central wall portion 142 toward wall portion 138 but each extends in a plane that, in the longitudinal direction, remains a generally constant distance from the plane of lower edge 118.

The wall portions 148 are located longitudinally between the ramps 130 and extend steeply to base wall portion 160 and define the transverse extending finger recess 126. Base wall portion 160 includes circular central portion 168. The upper surface 171 of central portion 168 is further from the plane of lower edge 118 than the surface 170 of base wall portion 160 surrounding circular central portion 168. Central portion 168 is a flow leader for moulding purposes and may be omitted.

As best seen in FIG. 19 the upper surface 170 of wall portion 160 is below the lowermost points of wall portions 140, 142 and so enables a user more easily to grasp an object located in the primary recess or finger recess. The lower surface 172 of base wall 160 is generally planar but slightly raised compared to lower edge 118.

The length of the tray is sized to enable a scalpel comprising a handle and blade to be stored temporarily in the tray. The user may place a scalpel on the ramps 130 with the blade edge facing the centreline. The scalpel then slides down the ramps 130 and falls into one or both of the primary instrument receiving recess 122 with the blade generally angled downwards and facing away from the user. The angled nature of the wall portions 140 and the central secondary recesses 144 assist in this, with the lower edge of the scalpel handle being more likely to be received in one or both of the central secondary recesses 144 and with the upper edge of the scalpel handle resting against one of the side walls portions 138.

A needle may be temporarily placed in the tray and located partially in one or more of the secondary recesses 144. The secondary recesses 144 are sized so that the point of a needle located in these secondary recesses cannot be contacted by a user merely by placing a finger on the side wall portions 140. Preferably the longitudinal length of the secondary recesses 144 is such that at least part (preferably the blunt rear end) of a standard medical needle will extend out of the secondary recesses and into the finger recess 126 so as to enable a user to grasp that part when needed.

Figure 20:
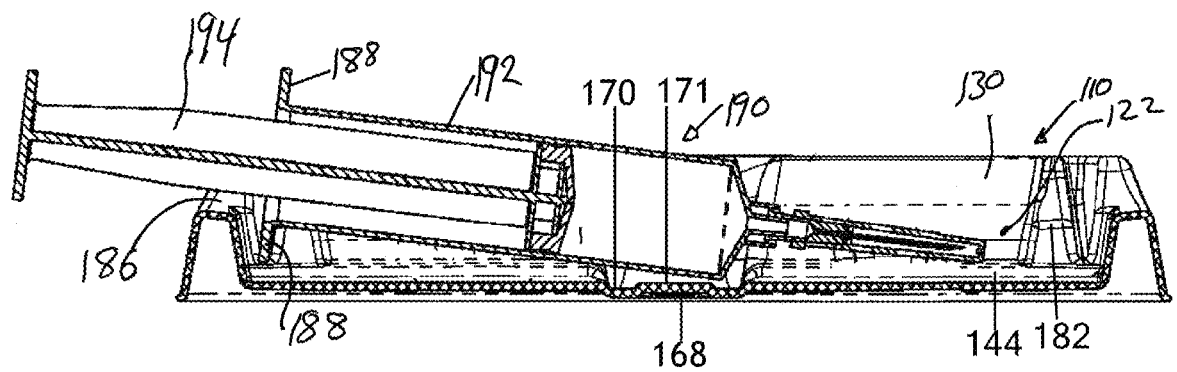
FIG. 20 is a side cross sectional view of the tray of FIG. 15 with a syringe.

As best seen in FIG. 16, the secondary recess 144 and instrument receiving recess 122 communicate with an instrument flange recess 180 that extends sideways from adjacent the end of the recesses 122 and 144. The instrument flange recess 180 is delineated from ramp 122 by wall portion 182 which has curved surface 184. The peripheral wall 116 has a curved instrument access opening 186 at the ends of the tray, as best seen in FIGS. 18 and 19. As best seen in FIG. 20, the instrument flange recess 180 is sized and shaped to accommodate the finger flanges 188 of a syringe 190, with the barrel 192 supported in the tray by finger flanges 188 and/or parts of the barrel 192 resting on curved surface 184 and/or other portion(s) of the tray and generally located in recesses between ramps 130. The curved instrument access opening 186 allows the plunger 194 to extend out of the tray.

The angled ramps 130 serve to aid in centring the syringe in the tray when initially placed in the tray.

Whilst the secondary recess 144 extends beyond the instrument receiving recess 122 and communicates with instrument flange recess 180, it will be appreciated that this is not critical and wall portion 182 may form a barrier between the secondary recess 142 and instrument flange recess 180, with wall portion 182 having a single continuous curved surface portion.

Unless the context clearly requires otherwise, throughout the description and any claims the words "comprise", "comprising", and the like are to be construed in an inclusive sense as opposed to an exclusive or exhaustive sense; that is to say, in the sense of "including, but not limited to".

The features of the invention described or mentioned in this document may be combined in any combination of features where features are not mutually exclusive.

It will be apparent to those skilled in the art that many obvious modifications and variations may be made to the embodiments described herein without departing from the spirit or scope of the invention.

The invention claimed is:

1. A medical tray adapted to receive a medical instrument, the tray having:
    a longitudinal axis;
    two longitudinally extending primary recesses having support surfaces adapted to receive and support at least a part of the medical instrument;
    a longitudinally extending finger recess located longitudinally between the two primary recesses and extending transversely from the longitudinal axis more than the primary recesses and sized to allow a user's finger to enter the finger recess either side of the primary recesses;
    a peripheral wall having a lower edge that lies in a first plane and an upper peripheral edge, at least one instrument access opening defined by the upper peripheral edge at a longitudinal end of the peripheral wall extending toward the first plane and with the remainder of the upper peripheral edge laying in a second plane;
    the peripheral wall surrounding the two primary recesses and the finger recess;
    at least one instrument flange recess located adjacent to and between the at least one instrument access opening and one of the primary recesses, the at least one instrument flange recess adapted to receive a flange of a medical instrument;
    the perpendicular distance of the closest part of the at least one instrument access opening to the plane being greater than the perpendicular distance of the closest part of the support surfaces to the plane;
    the finger recess having an upper surface adjacent the two primary recesses, the perpendicular distance of the upper surface from the plane being less than the perpendicular distance of the support surfaces adjacent the finger recess to the plane.

2. The tray of claim 1 wherein the at least one instrument flange recess is connected to the adjacent primary recess.

3. The tray of claim 2 wherein the at least one instrument flange recess extends transversely either side of the longitudinal axis more than the adjacent primary recess.

4. The tray of claim 3 wherein at least one of the primary recesses includes at least one secondary recess having a secondary surface adapted to receive and support a small medical instrument, including a needle.

5. The tray of claim 4 wherein the at least one secondary recess is located in a base section of the respective primary recess.

6. The tray of claim 1 wherein guide members extend transversely and upwardly from the primary recesses to the peripheral wall.

7. The tray of claim 5 wherein the perpendicular distance of the upper surface from the plane is less than the smallest perpendicular distance from the secondary surface to the plane.

8. The tray of claim 5 wherein the finger recess is adapted to receive a needle end of a syringe barrel.

9. The tray of claim 6 comprising a single finger recess and two instrument flange recesses.

10. The tray of claim 6 wherein the at least one primary recess comprises at least one set of primary recesses, each set comprising a first primary recess and a second primary recess.

11. The tray of claim 10 wherein the guide members comprise a first pair of guide member extending transversely from a first primary recess at a first angle and a second pair of guide members extending transversely from a second primary recess at a second angle.

12. The combination of a medical tray and a syringe, the tray having:
a longitudinal axis;
two longitudinally extending primary recesses having support surfaces adapted to receive and support at least a part of the syringe;
a longitudinally extending finger recess located longitudinally between the two primary recesses and extending transversely from the longitudinal axis more than the primary recesses and sized to allow a user's finger to enter the finger recess either side of the primary recess;
a peripheral wall having a lower edge that lies in a first plane and an upper peripheral edge, at least one instrument access opening defined by the upper peripheral edge at a longitudinal end of the peripheral wall extending toward the first plane and with the remainder of the upper peripheral edge laying in a second plane;
the peripheral wall surrounding the two primary recesses and the finger recess;
at least one instrument flange recess located adjacent to and between the at least one instrument access opening and one of the primary recesses, the at least one instrument flange recess adapted to receive a flange of a medical instrument;
the perpendicular distance of the closest part of the at least one instrument access opening to the plane being greater than the perpendicular distance of the closest part of the support surfaces to the plane;
the finger recess having an upper surface adjacent the two primary recesses, the perpendicular distance of the upper surface from the plane being less than the perpendicular distance of the support surfaces adjacent the finger recess to the plane,
the perpendicular distance of the closest part of the at least one instrument access opening to the plane being greater than the perpendicular distance of the closest part of the support surfaces to the plane;
the finger recess having an upper surface adjacent the two primary recesses, the perpendicular distance of the upper surface from the plane being less than the perpendicular distance of the support surfaces adjacent the finger recess to the plane,
and wherein the syringe comprises a hollow body with a finger flange, a plunger located in the hollow body and wherein the syringe is located in the tray with the finger flange located in the at least one instrument flange recess with the hollow body resting in or on at least one of the two primary recesses and with the plunger extending out of the tray through one of the at least one instrument access opening.

13. The combination of claim 12 wherein the finger recess is adapted to receive a needle end of the syringe barrel.

14. The combination of claim 13 wherein the primary recesses each include a secondary recess having a secondary surface adapted to receive a needle or cannula mounted on the syringe.

15. The combination of claim 13 wherein the at least one instrument flange recess is adapted to limit longitudinal motion of the syringe.

* * * * *